United States Patent [19]

Bahadir et al.

[11] Patent Number: 4,743,448

[45] Date of Patent: May 10, 1988

[54] ORGANIC CARRIER WITH INTEGRATED ACTIVE SUBSTANCES

[75] Inventors: Müfit Bahadir, Zolling; Gerd Pfister, Freising; Friedhelm Korte, Attenkirchen, all of Fed. Rep. of Germany

[73] Assignee: Gesellschaft für Strahlen- und Umweltforschung mbH, Neuherberberg, Fed. Rep. of Germany

[21] Appl. No.: 935,077

[22] Filed: Nov. 24, 1986

Related U.S. Application Data

[63] Continuation-in-part of Ser. No. 660,316, Oct. 12, 1984, abandoned.

[30] Foreign Application Priority Data

Oct. 15, 1983 [DE] Fed. Rep. of Germany ....... 3337592

[51] Int. Cl.$^4$ ...................... A01N 25/10; A01C 1/04; C08K 5/00
[52] U.S. Cl. ................................... 424/405; 424/406; 424/409; 424/414; 71/65; 71/76; 71/79; 71/3; 71/27; 71/64.02; 71/903; 71/904
[58] Field of Search ..................... 71/65, 76, 79, 3, 27, 71/64.02, 903, 904, DIG. 1; 424/405, 406, 409, 411, 414, 83

[56] References Cited

U.S. PATENT DOCUMENTS

| | | | |
|---|---|---|---|
| 3,454,510 | 7/1969 | Newland et al. | 424/29 |
| 3,864,114 | 2/1975 | Green | 71/3 |
| 3,864,468 | 2/1975 | Hyman et al. | 424/27 |
| 3,891,423 | 6/1975 | Stanley et al. | 71/79 |
| 4,350,678 | 9/1982 | Palvarini et al. | 424/27 |
| 4,411,683 | 11/1983 | Goertz | 71/903 |

OTHER PUBLICATIONS

Chem. Abstract 75:97577c, Van Breen, "Pesticidal Agent with Slow Material Output", p. 238, 1971.

*Primary Examiner*—Delbert R. Phillips
*Assistant Examiner*—Nathan M. Nutter
*Attorney, Agent, or Firm*—Spencer & Frank

[57] ABSTRACT

The present invention relates to a method for applying and using plant protection agents, preferably in agriculture and horticulture, in the form of sheets, webs and fabrics of organic material with integrated active substances. The integrated active substances slowly migrate from the polymer matrix and impose their effects at the point of application over an extended period of time. Such carrier/active substance combinations can be used as plant covers, mulches and for the production of stored crops.

12 Claims, 1 Drawing Sheet

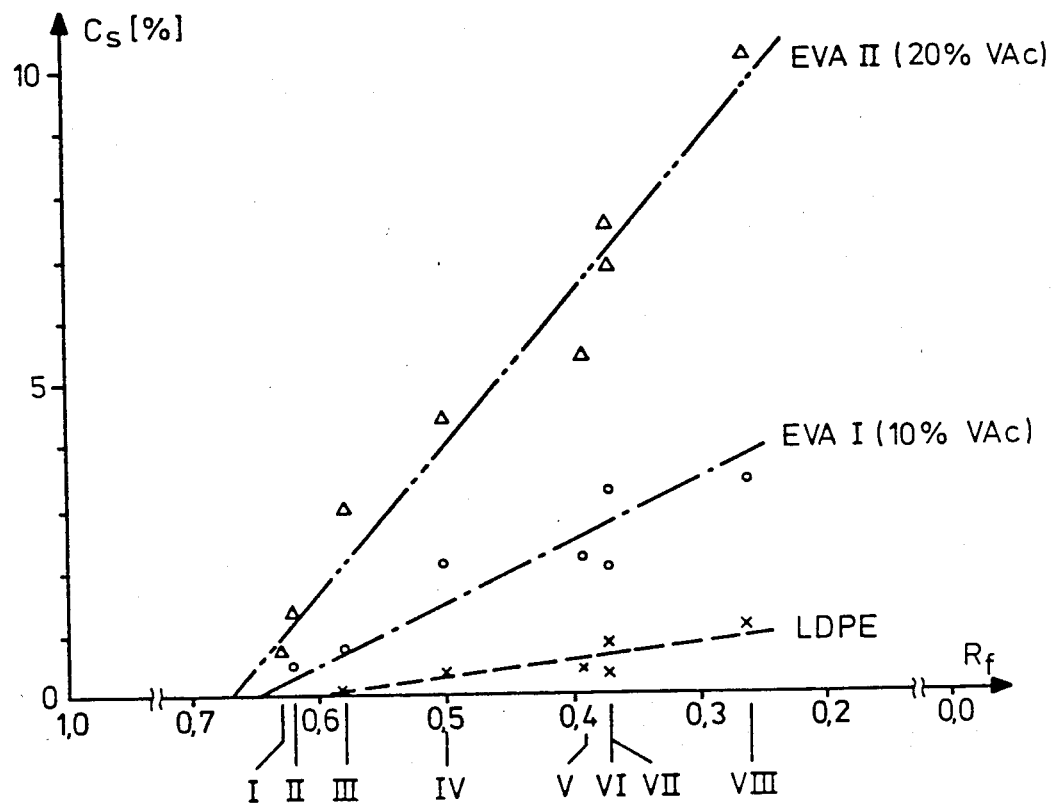

ORGANIC CARRIER WITH INTEGRATED ACTIVE SUBSTANCES

This application is a continuation-in-part of application Ser. No. 660,316, filed Oct. 12, 1984, now abandoned.

BACKGROUND OF THE INVENTION

The present invention relates to an organic carrier containing active substances for influencing plant growth and to a process for producing and using the same.

Plastic sheets are finding increased use in agriculture and horticulture for promoting growth and protecting crops. For example, perforated cover sheets have gained significant use in growing early vegetables and mulch sheets are used in cultivating corn and strawberries. By covering the plants, a microclimate is created under the sheets which, during the cold season in the spring, has noticeably higher temperatures than the uncovered surroundings and thus promotes growth. Simultaneously with promoting plant growth, however, the growth of undesirable weeds is encouraged. These weeds compete with the cultivated plants for light and nourishment, and prevent their proper development. Therefore, the weeds must be eliminated. In addition, fungus diseases such as powdery mildew and the like, as well as early damaging insects such as the cabbage maggot and the like, thrive in this humid and warm microclimate and must also be eliminated.

At present, insects and weeds are controlled by applying the necessary plant protection agents to the field before the sheets are applied, for example, by spraying solutions or dusts, and the sheets are then installed. Subsequent insect and weed control, after application of the sheets, is no longer possible. If one nevertheless desires to apply such agents, it becomes necessary to remove and reinstall the sheets, which makes the process uneconomical.

The period during which the cultivated plants are covered is generally two to three months. That means that the effect of the insect and weed control agents must be adapted to this period. With a one-time application before application of the sheets, the quantity of active substances must be selected to be correspondingly high to be effective over this long period of time without subsequent applications. However, excess quantities used in the application are subject to leaching, since weed killers and insecticides are water soluble to a certain extent. This results in the known problems of contaminating the soil and the groundwater and streams from which drinking water is obtained.

SUMMARY OF THE INVENTION

It is therefore an object of the present invention to develop formulations for articles by which, in the above-mentioned methods for growing plants under sheets, the use of plant protection agents is made compatible with the environment and any excess active materials is removed after one growing season or part thereof, i.e., one growth phase, since the sheet, web or fabric article contains no pro-oxidant constituent which would render it friable. Moreover, such formulations are not limited to very few plant protection agents but are available for general use during one growing season or phase, although the articles may be reinstalled for the next growing season or phase, if their active ingredients have not been spent and/or if otherwise useful. Economy of operation is assured as known technologies can be applied.

According to the present invention, this is accomplished by using an organic carrier matrix containing active agents that are released over time to aid the growth of selected plants. The carrier matrix is made from organic polymers and includes the active agents within its structure. These agents may be plant protection agents, growth promoters, growth inhibitors, synergists, and adjuvants which are mixed with the polymer before it is formed into the sheets, filaments or webs from which the covering material is made. The environment is protected from contamination by excess active material by removing the covering method after one growing season or phase thereof as is appropriate to the nature of the crop to be grown and the active ingredient itself. Thus, cultivated areas may be covered only during the sprouting of seed phase for a period spanning, for example, several weeks; during the plant cultivation period from planting up to harvesting for a period spanning, for example, from two to three months; or in the case of winter crops, over the winter for a period spanning, for example, nine or ten months.

BRIEF DESCRIPTION OF THE DRAWING

The FIGURE is a graph presenting the saturation concentrations of the active substances in various polymers as a function of relative polarity.

DETAILED DESCRIPTION OF THE EMBODIMENTS

In the concept of the present invention, the organic carrier material is understood to include matrixes of organic polymers in which active substances and adjuvants can be integrated and which can be processed into sheets, webs or fabrics. Suitable carriers are thus organic polymers, e.g. homopolymers and copolymers of substituted and unsubstituted alpha olefins, polymerized with themselves or with other compounds, such as polyethylene, polypropylene, polybutene, polystyrene, polymethylpentene, ethylene vinyl acetate, ethylene ethyl acrylate, polyisoprene, polybutadiene, copolymers of ethylene with higher alpha olefins and others; polycondensates or polyadducts, e.g. polyamides, linear polyurethanes, linear polyesters, polycarbonates, polyacetates, polyethers and others; or modified natural products, e.g. hydrated cellulose, cellulose esters, cellulose ethers, latex, linoxyn, Factice (for vulcanized vegetable oils) and others.

Plant protection agents within the concept of the present invention are understood to include insecticides, acaricides, nematicides, repellants, fungicides, herbicides, rodenticides, and mulluscicides, as well as growth promoters and inhibitors and synergists. The chemical origin of these active substances is not critical. They may originate from the most varied classes of chemical compounds. The only requirement is that they must be stable under the manufacturing conditions for the carrier/active substance combinations. Thus, compounds from, for example, the chemical classes of the chlorocarbons (lindane and others), organophosphorus acid esters (parathion and others), carbamates (carbofuran and others), cyclodiene derivatives (endosulfan and others), pyrethroides, pyrethrins (cypermethrin and others), xanthogenates (dixanthogen and others), triazole derivatives (azocyclotin and others), organic sulfides (chlorfen sulfide and others), metal-organic compounds (cyhexatin and others), thiadiazine derivates (dazomet and others), phthalates (dimethylphthalate and others), morpholine derivatives (aldimorph and others), triazine derivatives (desmetryn and others), anilides (benodanil and others) imidazoles (benomyl and others), phthalimide derivatives (captan and others), sulfamides (dichlofluanid and others), pyrimidine derivatives (dimethirimol and others), thiadiazols (etridiazol and others), polymeric dithiocarbamates (maneb and others), monomeric dithiocarbamates (sulfallate and others), oxazolidine derivatives (vinchlozolin and others), urea derivatives (monolinuron and others), benzoic acid derivatives (chlorothiamid, dichlobenil and others), phenoxyalkane acid derivatives (2,4-D and others), aryl alkane acid derivatives (Fenac (for 2,3,6-trichlorophenyl acetic acid) and others), aniline derivatives (fluchloralin and others), uracil derivatives (lenacil and others), pyridazone derivatives (chloridazon and pyrazon and others), thiourea derivatives (ANTU and others), coumarin derivatives (coumafuryl and others), aryl alkanol derivatives (ancymidol and others), indolyl derivatives (indolylacetic acid and others), dialkane acid derivatives (maleic acid hydrazide and others), chloralkane ether derivatives (octachlorodipropyl ether and others), and sulfoxide derivatives (sulfoxides and others) can be used in accordance with the present invention.

The combinations of carriers and active substances can be manufactured according to known processes. For thermoplastic carriers, worm extruders are used with preference in the production of these formulations. For this purpose, polymer granules, plant protection agents and any required adjuvants are premixed and plasticized in worm extruders and then processed into sheets, webs or fibers for fabrics. If liquid substances are incorporated in organic polymers in single worm extruders without positive feed, discharge may be interrupted since the liquid may act as a lubricating film and impede conveyance of the granules. In such cases, the present invention provides that some or all of the polymer granules are substituted by other powdered adsorbents, such as, for example, fine particulate silica gels or kieselguhr, whereupon conveyance through the extruder will again take place without problems.

The timed release of the plant protection agents from the combination of carrier and active substances is determined by both the type of carrier and the polarity of the active substances. The quantities of active substances incorporated in the carrier matrix are subject to the same restrictions. Thus, an accurate determination of the polarity of the active substances relative to the polymers employed is of central significance.

A particularly simple and effective method for predetermining the suitability of carrier/active substance combinations for use in the present invention is by determining the Rf values of the plant protection agents using phase reversal thin layer chromatography (RP-TLC). The Rf values determined indicate a relative polarity series which corresponds to the solubilities of the plant protection agents in the carrier/active substance combinations according to the present invention. The Rf-value (retention or retardation factor) is calculated as the travel-distance of the substance-spot divided through the travel distance of the solvent front on the thin layer plate.

The drawing illustrates the saturation concentrations ($C_s$) of the plant protection agents in sheets (70 microns thick) in dependence on their relative polarities, determined by RP-TLC ([$C_{18}$, 75% by volume, $CH_3CN$ in $H_2O$].

I: metoxuron
II: DDVP
III: monolinuron
IV: desmetryn
V: chlorfenvinphos
VI: lindane
VII: parathion
VIII: endosulfan ($\overline{\alpha+\beta}$).

If $C_{18}$ phases are used in conjunction with acetonitrile/water=75/25 (vol/vol), plant protection agents whose Rf values lie in a range between 0.1 and 0.8, preferably between 0.2 and 0.7, are particularly suitable.

If adjuvants are required for the production or application of the carrier/active substance combinations, such adjuvants can be added to the starting mixtures during production of the formulations and can be processed together with the active substances. Such adjuvants are primarily polymer additives which simplify processing or protect the formulation at the location of application. Such adjuvants preferably originate from the class of antioxidants (e.g. bisphenols, hydroxybenzyl compounds, 4-hydroxyanilides, amines, thioethers, phosphites and others), light protection agents (e.g. 2-hydroxybenzophenone, 2-hydroxyphenylbenzotriazole, nickel-organic compounds, acid esters, sterically blocked amines and others), lubricants (e.g. fatty alcohols, dicarboxylic acid esters, fatty acid esters, fatty acids, fatty acid soaps, fatty amides, montanic acids, montanic acid esters, paraffins, polyethylene waxes and others), softeners (e.g. esters of phosphoric acids, phthalic acids, fatty acids, alkane acids, dicarboxylic acids, sulfonic acids, sulfamides, alcohols, ethers, ketones, hydrocarbons and others), antistatic agents (e.g., quaternary ammonium salts, phosphonium salts, sulfonium salts, alkyl sulfonates, alkyl sulfates, alkyl phosphates, alkyl dithiocarbamates, alkyl carboxylates, polyethylene glycol esters, polyethylene glycol ethers, fatty acid esters, fatty acid ethanol amides, glycerides, fatty amines and others) and pigments and fillers (inorganic and organic dyes or fillers such as carbonates, silicates, sulfates, graphite, fibers, color pigments and others).

Such carrier/active substance combinations can be used for covering the ground or plant cultures, or both. By controlling deleterious organisms and/or regulating the growth of the cultivated plants, the growth of agricultural and horticultural crops is promoted. Due to the time controlled release of the active substances from these formulations, excess concentration of the active substances in the plant system or ground is reduced and problems with undesirable residues are prevented. The retarded release of the active substances is caused by the necessary diffusion controlled migration through the polymeric matrix to the surface of the formulation, from where they are removed by their volatility or by dissolution in rain or dew or by direct contact with target organisms.

Such formulations are also suitable for the protection of stored crops. If the harvested material (e.g., seed) is stored in sacks made from the carrier/active substance combinations, the harvested material can be effectively protected against deleterious organisms. For harvested material intended for human consumption, multilayer containers are better suited if the innermost container layer is made of a material free from the active substances. This effectively prevents inadvertent contamination of the harvested material by the active substances in the outer container layers.

The effectiveness of carriers made from organic materials having integrated active substances for use in agriculture and horticulture will be demonstrated with the aid of the following examples.

In all examples, the following commercially available LDPE and EVA granules were employed:

LDPE: MFI 190/2.16=0.55 g/10 min; density 0.921 g/cm$^3$

EVA I: 10% VAc; MFI 190/2.16=0.55 g/10 min; density 0.926 g/cm$^3$

EVA II: 20% VAc; MFI 190/2.16=2 g/10 min.; density 0.939 g/cm$^3$

MFI (Melt Flow Index) means the amount of a thermoplastic polymer in grams, which is pressed out of a die with 1.8 mm in length and 2.08 mm diameter in the time of usual 10 min by a certain loaded weight. E.g. MFI 190/2.16=0.55/10 min means 0.55 g of the melt at 190° C. is pressed out in 10 min by a weight of 2.16 kg.

VAc means Vinylacetate.

In the examples in which these polymers are used in the form of powders, the powders were produced from the abovementioned granules by cold grinding and therefore have the same characteristics.

EXAMPLE 1

5 g powdered lindane and 95 g LDPE granules were mixed by stirring for 1 hour in a 1 liter round-bottom flask. This mixture was filled into the intake funnel of a single worm extruder (20 mm diameter of 25 D*), broad slit orifice: 100 mm×0.5 mm, sheet removal) having four heating zones heated to 150° C. and operating at 25 rpm to produce flat sheets having a thickness of 70 microns. For reasons of industrial hygiene, the extruder was placed in an inspectable fume chamber and the region between the orifice and the sheet discharge was also completely enclosed and separately vented.

*)20 mm o×25 o is the usual abbreviation for extruder screw dimensions. In this case it means a screw with 20 mm diameter and a length of 25 diameters (D).

Approximately 24 hours after extrusion, the surface of 5 g (about 8.5 cm×80 cm) of the resulting sheet was washed briefly (about 30 seconds) with methanol to isolate the active substance that sweated-out during extrusion. The washed sheet was extracted with hexane for 12 hours in a Soxhlet extractor to isolate the amount of the active substance that had been incorporated in the polymer.

The quantity of the resulting lindane was determined by way of capillary gas chromatography (FID).

Sweated-out quantity of active substance: 3.88%
Incorporated quantity of active substance: 0.31%
Total recovery of active substances: 83.40%

The total recovery of active substances is calculated from the summed amounts of sweated out and incorporated quantities of active substance, compared with the amount, that had been added to the polymer before extrusion.

EXAMPLE 2

The procedure was the same as in Example 1. 5 g lindane and 95 g EVA I were used.

Sweated-out quantity of active substance: 2.79%
Incorporated quantity of active substance: 2.03%
Total recovery of active substance: 96.40%

EXAMPLE 3

The procedure was the same as in Example 1. 10 g lindane and 90 g EVA II were used.

Sweated-out quantity of active substance: 1.05%
Incorporated quantity of active substance: 7.75%
Total recovery of active substance: 88.00%

COMPARATIVE EXAMPLES 1-3

In these comparative examples it was demonstrated that high incompatibility of the active substance with the polymer caused difficulties during extrusion and achieved very poor incorporation rules of active substances.

The procedure was the same as in Example 1. 5 g metoxuron were used with 95 g of (1) LDPE, (2) EVA I, (3) EVA II. Movement of this mixture through the worm extruder stopped again and again. Occasionally active substances in the liquid state were ejected from the orifice and the sheet tore frequently.

In the active substance determination with the aid of HPLC (5 μg RP-18, inner diameter 5 mm, length 100 mm, UV detector, MeOH/H$_2$O), only the following incorporated quantities of active substance were determined:
(1) <<0.1%;
(2) 0.12%;
(3) 0.75%.

EXAMPLES 4-6

In these Examples it was demonstrated how liquid active substances are processed.

The procedure was the same as in Example 1, with the difference that the active substance chlorfenvinphos was liquid. The following quantities were used:

(4)
2 g chlorfenvinphos,
88 g LDPE granules and
10 g LDPE powder;

(5)
5 g chlorfenvinphos,
85 g EVA I granules and
10 g LDPE EVA I powder;

(6)
10 g chlorfenvinphos,
80 g EVA II granules and
10 g EVA powder.

Extrusion posed no problems. An analysis of the resulting sheets indicated the following quantities of incorporated chlorfenvinphos:
(4) 0.39%;
(5) 2.2%;
(6) 5.38%.

COMPARATIVE EXAMPLES 4-6

In these comparative examples it was demonstrated that without the presence of polymer powder, the extrusion of liquid active substances into sheets was impossible.

The procedure was the same as in Examples 4-6, with the difference that the polymer powders were replaced by granules. The quantities of active substances remained unchanged. Mixing of the chlorfenvinphos with the granules results in sticky-tough agglomerations of granules which were not transported by the extruder worm. Thus no sheets could be obtained.

EXAMPLES 7-9

In these examples it was demonstrated that plant protection agents having a melting point above the extrusion temperature and low solubility in the polymer matrix could be incorporated in the sheets in the form of a dispersion. This dispersed particles should not exceed the thickness dimension of the sheets. They may preferably be in the range of less than half the sheet thickness.

The procedure was the same as in Example 1.

2 g of chloridazon (pyrazon, Fp=205° C.) were used together with 98 g of (7) LDPE, (8) EVA I and (9) EVA II. Extrusion posed no problems, and sheets were obtained which contained dispersed chloridazon. The chloridazon, which is only slightly soluble in n-hexane, was extracted from the sheets with chloroform, transferred to methanol, where the likewise dissolved polymer was flocculated out. The quantity of active substance in methanol solution was determined by HPLC. The initial quantities of active substances were accounted for.

EXAMPLES 10-27

These examples demonstrate, for a further selection of plant protection agents, the broad applicability of including plant protection agents within polymer formulations in sheets.

The procedures were the same as in preceding Examples 1 through 6. Experimental conditions and results are listed in Table 1.

The following examples relate to the use in early vegetable production of sheets containing plant protection agents according to the present invention and produced in the embodiments of Examples 1-27. The sheets equipped with the herbicide desmetryn were used in the form of flat sheets having a thickness of 70 microns, as described in Example 1, which are welded together in the longitudinal direction until a width of 1.20 m was obtained. EVA I (10% VAc) was used. 500 holes each having a diameter of 1 cm were punched into every m² of these welded-together broad strips of sheet. A comparison sheet without active substances was produced in the same manner from EVA I.

COMPARATIVE EXAMPLE 7

This comparative example demonstrates the normal growth of cultivated plants, indicator plants and weeds under covering sheets in a test field.

Each of four tests parcels of land measuring 1 m×2 m was planted on Apr. 13, 1983, with 15 cabbage seedlings. In the same parcels, 50 seeds of lettuce, watercress and mustard were sown as indicator plants, sensitive to desmetryn, and the parcels were covered with EVA I sheets free of active substances.

When the covers were removed on May 19, 1983, the following average plant inventory was taken per parcel:

| | | | |
|---|---|---|---|
| cabbage: | 13.5 plants | (90%) = | 12.8 g dry matter |
| lettuce: | 20.8 plants | (42%) = | not determined |
| watercress: | 39.8 plants | (80%) = | 8.7 g dry matter |
| mustard: | 41.5 plants | (83%) = | 13.7 g dry matter |
| weeds: | 316.0 plants | | not determined |

EXAMPLE 28

This example demonstrates that the desmetryn containing cover sheet does not hurt the cultivated plant (cabbage) but effectively suppresses desmetryn sensitive indicator plants and weeds.

Four test parcels measuring 1 m×2 m, adjacent to those of Comparison Example 7 were planted and seeded during the same test period as Comparison Example 7 and covered with EVA I sheets containing 0.2% desmetryn. Upon removal of the sheets, the following results were recorded:

| | | | |
|---|---|---|---|
| cabbage: | 14.6 plants | (97%) = | 12.7 g dry matter |
| lettuce: | 0.8 plants | (2%) = | not determined |
| watercress: | 0 plants | (0%) = | 0.0 g dry matter |
| mustard: | 15.5 plants | (31%) = | 3.2 g dry matter |
| weeds: | 89.2 plants | | not determined |

If one relates these results to the O-parcels covered with the comparison sheet of EVA I containing no active substances, the following results are obtained:

| | |
|---|---|
| cabbage: | 108% plants with reference to the O-parcels |
| lettuce: | 4% plants with reference to the O-parcels |
| watercress: | 0% plants with reference to the O-parcels |
| mustard: | 37% plants with reference to the O-parcels |
| weeds: | 28% plants with reference to the O-parcels |

COMPARATIVE EXAMPLE 8

This comparative example demonstrates that the use of too large a concentration of desmetryn also interferes with the growth of the cultivated plants.

This comparative example was set up and conducted according to Comparative Example 7 and Example 28, with the difference that the EVA I sheets contained 1% desmetryn.

After initial sprouting, all plants in these parcels died after exhibiting chlorosis.

EXAMPLE 29

This example demonstrates that the pesticide containing sheets according to the present invention are likewise suitable as mulching sheets.

Each of four test parcels measuring 1 m×2 m, likewise adjacent to the parcels of Comparison Example 7, was seeded on Apr. 25, 1983, with 50 seeds of lettuce, watercress and mustard, and the parcels were covered with EVA I sheets containing 2% desmetryn. In addition to the already described 500 holes per m², these sheets also contained 10 additional holes of 20 cm². Ten cabbage seedlings were planted into these holes so that the plants were disposed primarily above the covering sheets. When the sheets were removed after 24 days, on May 19, 1983, 50% of the cabbage plants had developed while all of the indicator plants and weeds, after initial sprouting, had died.

Although the desmetryn concentration in the mulching sheets was twice that of Comparative Example 8, half of all cultivated plants survived. This demonstrates the lack of influence of the active substance on the cultivated plants above the sheet cover, while all indicator plants and weeds below the sheets were effectively prevented from growing.

TABLE I

Experimental Conditions and Results for Examples 10–27

| Example | Plant Protection Agent | → | Quantity Used (g) | Quantity of Polymer Used (g) | | Extraction Agent | Determination Method | Quantity of Active Substance Incorporated (%) |
|---|---|---|---|---|---|---|---|---|
| | | | | Granules | Powder | | | |
| 10 | Endosulfan($\alpha\beta$) | | 5 | LDPE 95 | — | n-Hexan | GC | 1.07 |
| 11 | Endosulfan | | 5 | EVA I 95 | — | n-Hexan | GC | 3.37 |
| 12 | Endosulfan | | 10 | EVA II 90 | — | n-Hexan | GC | 10.20 |
| 13 | DDVP | | 2 | LDPE 88 | 10 | n-Hexan | GC | 0.07 |
| 14 | DDVP | | 2 | EVA I 88 | 10 | n-Hexan | GC | 0.51 |
| 15 | DDVP | | 5 | EVA II 85 | 10 | n-Hexan | GC | 1.33 |
| 16 | Parathion | | 2 | LDPE 88 | 10 | n-Hexan | GC | 0.76 |
| 17 | Parathion | | 5 | EVA I 85 | 10 | n-Hexan | GC | 3.25 |
| 18 | Parathion | | 10 | EVA II 80 | 10 | n-Hexan | GC | 6.86 |
| 19 | Monolinuron | | 2 | LDPE 98 | — | Chloroform | HPLC | 0.10 |
| 20 | Monolinuron | | 5 | EVA I 95 | — | Chloroform | HPLC | 0.80 |
| 21 | Monolinuron | | 5 | EVA II 95 | — | Chloroform | HPLC | 3.00 |
| 22 | Desmetryn | | 2 | LDPE 98 | — | Chloroform | GC | 0.35 |
| 23 | Desmetryn | | 5 | EVA I 95 | — | Chloroform | GC | 2.10 |
| 24 | Desmetryn | | 5 | EVA II 95 | — | Chloroform | GC | 4.40 |
| 25 | Dichlofluanid | | 2 | LDPE 98 | — | Chloroform | GC | 0.05 |
| 26 | Dichlofluanid | | 3 | EVA I 97 | — | Chloroform | GC | 0.16 |
| 27 | Dichlofluanid | | 5 | EVA II 95 | — | Chloroform | GC | 2.36 |

It will be understood that the embodiments described above are provided for purposes of illustration only. The invention is intended to include all modifications and equivalences within the boundaries of the appended claims.

We claim:

1. An article of manufacture in the form of a sheet, web, or fabric for use in growing plants, said article comprising an organic carrier matrix and at least one active substance formulated integrally within said organic carrier matrix whereby a time controlled release of said at least one active substance from said composition of matter is obtained by a diffusion controlled migration of said at least one active substance through said organic carrier matrix to the surface of said article; wherein said organic carrier matrix comprises one or more organic polymer, wherein said at least one active substance comprises one or more agents selected from the group consisting of plant protection agents, plant growth promoters, plant growth inhibitors, synergists, adjuvants, and mixtures thereof, and wherein said article is stable under plant growing conditions, contains no pro-oxidant constituent, and is removed after one growing season or part thereof.

2. The article defined in claim 1, which is perforated or partially perforated.

3. The article defined in claim 2, which has holes therein of sufficient size for selected plants to protrude.

4. A container for storing harvested crops for preventing damage to the stored crop by deleterious organisms comprising the article defined in claim 1.

5. An article of manufacturer in the form of a sheet, web, or fabric for use in growing plants, said article comprising an organic carrier matrix and from about 0.1 to 20 weight percent of at least one active substance formulated integrally within said organic carrier matrix whereby a time controlled release of at least one said active substance from said composition of matter is obtained by a diffusion controlled migration of said at least one active substance through said organic carrier matrix to the surface of said article; wherein said organic carrier matrix comprises one or more organic polymers, wherein said at least one active substance comprises one or more agents selected from the group consisting of plant protection agents, plant growth promoters, plant growth inhibitors, synergists, adjuvants, and mixtures thereof, wherein the at least one active substance has an Rf value, which, when determined by phase reversal thin layer chromotography with $C_{18}$ phases, developed in an acetonitrile/water combination of 75/25 volume ratio, is between about 0.1 and 0.8, and wherein said article is stable under plant growing conditions, contains no pro-oxidant constituent, and is removed after one growing season or part thereof.

6. The article defined in claim 5, wherein the Rf value of the at least one active substance is between about 0.2 and 0.7.

7. The article defined in claim 5, wherein the at least one active substance is present in a concentration between about 0.1 and 10 weight percent.

8. The article defined in claim 1, wherein the organic matrix comprises one or more organic polymers selected from the group consisting of polymers of addition, condensation polymers, and modified natural polymers.

9. The article defined in claim 8, wherein the organic polymers are selected from the group consisting of alpha-olefin polymers, polyamides, polyurethanes and cellulose esters.

10. The article defined in claim 1, wherein the plant protection agents are one or more agents selected from the group consisting of insecticides, acaricides, nematicides, repellants, fungicides, herbicides, rodenticides and molluscicides.

11. The article defined in claim 1, wherein the adjuvants are one or more additives selected from the group consisting of antioxidants, light protection agents, lubricants, softeners, antistatic agents, pigments and fillers.

12. The article defined in claim 1, in a form selected from the group consisting of a mulching ground cover, a plant cover, a tunnel cover and a greenhouse cover.

* * * * *